(12) United States Patent
Zhang et al.

(10) Patent No.: US 6,340,773 B1
(45) Date of Patent: Jan. 22, 2002

(54) PREPARATION OF HALOGENATED PRIMARY AMINES

(75) Inventors: Mingbao Zhang, Morris County; Michael A. Kocur, Union County; Mary Frances Martin, Bergen County, all of NJ (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/396,686

(22) Filed: Sep. 14, 1999

(51) Int. Cl.[7] ............... C07C 211/03; C07C 209/40
(52) U.S. Cl. ............... 564/384; 564/336; 564/385
(58) Field of Search ............... 564/336, 345, 564/384, 385

(56) References Cited

FOREIGN PATENT DOCUMENTS

| EP | 0 548 897 A | 6/1993 |
|---|---|---|
| EP | 0 696 576 A | 2/1996 |

OTHER PUBLICATIONS

Wang et al, J. Org. Chem., vol. 50, No. 25, pp 5448–5450, 1985.*

Negi et al, Synthesis, pp 991–996, 1996.*

Konz et al, Heterocycles, vol. 29, No. 4, pp 691–706, 1989.*

Fr. Bergel Et Al.: "Aryl–2–halogenoalkylamines. Part XV. Some Cationic and Basically Substituted Aryl Compounds", Journal of The Chemical Society., 1955, pp. 3835–3839.

Chemical Abstracts, vol. 82, No. 13, Mar. 31, 1975, Columbus, Ohio, US; abstract No. 86178s.

D. Mravec Et Al.: "4–Bromobenzonitrile Catalytic Hydrogenation Under Pressure", p. 505, column 1; XP002155167 abstract & Zb. Pr. Chemickotechnol. Fak Svst 1972, 1974, pp. 231–236.

* cited by examiner

Primary Examiner—Shailendra Kumar
(74) Attorney, Agent, or Firm—Colleen Szuch; Steve Driscoll

(57) ABSTRACT

A method of preparing a halogenated primary amine comprising hydrogenating a halogenated oxime in the presence of a catalyst comprising a non-palladium noble metal or a base metal under conditions sufficient to produce a halogenated primary amine.

26 Claims, No Drawings

PREPARATION OF HALOGENATED PRIMARY AMINES

FIELD OF INVENTION

The present invention relates to the preparation of halogenated amines. More specifically, this invention relates to the preparation of halogenated benzylamines.

BACKGROUND OF THE INVENTION

Halogenated benzylamines, such as bromobenzylamine, are used commonly in the synthesis of fine organic chemicals for use in products in the pharmaceutical, flavor and fragrance, and agricultural fields just to name a few. Halogenated benzylamines are especially useful as stating materials and intermediates given the relatively high reactivity of their halogen group functionality. For example, bromobenzylamine is particularly useful because its bromine functionality acts as a leaving group allowing complex amines to be formed. Therefore, given the desire for halogenated amines, there is a corresponding need for economic and practical methods of synthesizing these compounds. The present invention fulfills this need among others.

DESCRIPTION OF THE INVENTION AND PREFERRED EMBODIMENTS

The present invention provides for the preparation of halogenated amines through the catalytic hydrogenation of a corresponding halogenated oxime. Although catalytic hydrogenation of oximes to form amines is well known, traditional reactions tend to be harsh and generally involve the use of highly active catalysts such as palladium. Under these conditions, traditional catalytic hydrogenation results in concurrent dehydrohalogenation and thus is generally inapplicable to the preparation of halogenated amines.

It has been found surprising, however, that using a catalyst based on either noble metals other than palladium or base metals minimizes dehydrohalogenation. Despite being generally less reactive than palladium, these catalysts nevertheless effect commercially-acceptable reaction rates and high yields. Moreover, it has been found that suitable results are obtained under mild, ambient reaction conditions. Such mild conditions not only help to minimize dehydrohalogenation, but also make hydrogenation of the halogenated oxime relatively convenient.

It also has been found surprisingly that the catalyst is reusable in subsequent hydrogenation reactions. Indeed, the effectiveness of the catalyst tends to improve with reuse until reaching a steady state condition.

Accordingly, the present invention provides for a highly-effective, low cost, simple and convenient approach for preparing a wide variety of halogenated amines.

One aspect of the present invention is a method of preparing a halogenated amine using a catalyst based on a suitable non-palladium noble metal or a base metal. In a preferred embodiment, the method comprises hydrogenating a halogenated oxime in the presence of a suitable non-palladium noble metal-based catalyst or base metal-based catalyst and under conditions sufficient to produce a halogenated primary amine.

The catalyst should be adequate to promote the reaction, however, it should not be so active as to break the halogen/carbon bond. It has been found that catalysts comprising a suitable non-palladium nobel metal or a base metal are suitable to effect such a reaction. Preferred non-palladium nobel metals include, for example, iridium, rhodium, ruthenium, platinum, oxides thereof, and combinations of two or more thereof. Preferred base metals include, for example, nickel, cobalt, oxides thereof, and combinations of two or more thereof. More preferably, the catalyst comprises platinum and/or rhodium including alloys therewith or oxides thereof. Even more preferably, the catalyst comprises platinum and/or oxides thereof.

The non-palladium nobel metal and/or a base metal may be used as a catalyst in its pure form, for example, as a wire, although preferably it is deposited on a conventional support. The amount of metal deposited on the support may vary, and suitable results are achievable with a catalyst comprising about 1 to about 10% metal by weight, and, preferably, about 5% by weight.

The material used for the support can vary and are readily-determinable by one skilled in the art. Preferred materials include, for example, charcoal, aluminum, and the like. Preferably, the support is charcoal. Suitable forms of the support include, for example, powders, granules and pellets. Preferably, the catalyst comprises a readily-filterable form, such as, powder.

Suitable commercially-available catalysts are available from Engelhard Corporation (Beachwood, Ohio) as product nos. 781A-15-1 and 781A-15-6-1; and from Johnson Matthey (West Deptford, N.J.) as product nos. B21142-1.5, B21137-3, B21101-5, B21159-5, B21142-5, C21190-5 and C21108-5

Loading of the catalyst in the reaction can be determined readily by one skilled in the art. Generally, a concentration of catalyst metal to starting material of about 0.1 to about 10 wt. % is preferred, and a concentration of about 0.5 to about 4 wt. % is more preferred. At concentrations below 0.5 wt. %, reaction rates tend not to be commercially viable while, at concentrations above 4 wt. %, the amount of catalyst used becomes prohibitively expensive and filtering thereof becomes significant.

The hydrogenation is conducted under conditions sufficient to react a halogenated oxime with hydrogen to produce a halogenated amine. Such conditions are readily achievable since it has been found that the reaction occurs at a sufficient rate and with sufficient selectivity at ambient conditions. Specifically, the reaction may be conducted at or near atmospheric pressure and at about room temperature. Although ambient conditions are preferred from a convenience standpoint, conducting the reaction over a wide range of pressures and temperatures, for example, from about 1 to about 10 atm and from about 5 to about 100° C., is within the scope of invention.

The hydrogen may be supplied to the reaction in any known manner. For example, the reaction mixture may be sparged or blanketed with hydrogen. In any event, the supply of hydrogen should be sufficient to sustain the reaction. It has been found that supplying the hydrogen to the reaction at a pressure of about 1 to about 10 atm.

To improve the selectivity of the reaction, an anhydrous environment is preferred. More specifically, it has been found that water in the reaction mixture tends to result in the formation of secondary and tertiary amines which are undesirable. Accordingly, it is preferred that efforts be taken to establish a substantially anhydrous environment. The term "substantially anhydrous" as used herein means that the reaction mixture contains less than about 0.1 wt. % water and preferably contains less than about 0.05 wt. % water. To this end, it is preferred to use an organic solvent. Suitable organic solvents include, for example: alcohols such as ethanol, methanol, and isopropanol; acidic solvents such as acetic acid and propionic acid; and anhydride solvents such as acetic anhydride. In a preferred embodiment, the organic solvent is an alcohol, more preferably, ethanol.

In addition to using an organic solvent to provide for a substantially anhydrous reaction mixture, it may be necessary to "dry" the catalyst. That is, suitable catalysts are typically available in the form of a wet paste to minimize the risk of fire/explosion. This paste typically contains from about 30 to about 60% by weight water. To dry the catalyst paste, it is preferred to perform a solvent exchange with the water. Solvent exchange is a well-known process and may be performed using an organic solvent as described above.

To render the amine stable and to prevent it from contaminating or "poisoning" the catalyst, it is generally preferred to combine it with another substance. Although one skilled in the art can identify a variety of ways of combining the amine with another substance to stabilize it, forming a salt with a mineral acid is preferred such that its interaction with the catalyst is minimized. For handling convenience, it is generally preferred to maintain the halogenated amine in its combined form to avoid oxidation in air. For example, as a salt, the halogenated amine is a stable solid as opposed to a less-stable liquid in its pure form. Unless otherwise indicated the term "halogenated amine" as used herein refer both to the halogenated amine's pure and combined forms.

It has been found that under the reaction conditions of the present invention, ferrous-containing reactors undergo significant corrosion which tends to deactivate the catalysts used. Therefore, in the preferred embodiment, the reaction is conducted in a non-ferrous or low-ferrous content reactor. Suitable reactors include, for example, glass/glass-lined vessels, Teflon/Teflon-lined vessels, and Hastelloy C vessels.

Recovery of the halogenated amine (or a salt thereof as described above) from the reaction mixture is relatively straightforward and involves known techniques, such as crystallization and filtration. Preferably, after hydrogenation, the reaction mixture is filtered to remove the catalyst (which is reusable as described below) and then the halogenated amine is isolated through crystallization. Crystallization is well known in the art and involves concentrating the solution containing the halogenated amine to precipitate it in its combined form. The mother liquor from one such crystallization step then may be subjected to additional crystallization steps to extract nearly all of the halogenated amine from the reaction mixture.

Another important benefit of the present invention is the ability to reuse the catalyst. Indeed, it has been found that the catalyst not only is reusable, but also improves with use until reaching a steady state. Therefore, in the preferred embodiment, after the catalyst is separated from the reaction mixture, it is cleated by washing with a non-aqueous solvent, for example, an organic solvent as mentioned above, and reused.

In a preferred embodiment, the synthesis method of the present invention is used in hydrogenating a halogenated oxime having a formula:

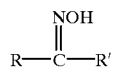
(1)

to form a halogenated amine having the formula:

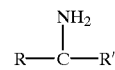
(2)

wherein:
R and R' are independently selected from hydrogen, unsubstituted or substituted aliphatic radicals, or an unsubstituted or substituted aromatic radicals, providing that R or R' comprises at least one halogen.

In Formulas (1) and (2), R and R' preferably are selected independently from hydrogen, unsubstituted or substituted $C_6$–$C_{15}$ aromatic radicals, unsubstituted or substituted $C_1$–$C_{10}$ aliphatic radicals, or unsubstituted or substituted $C_3$–$C_{10}$ alicyclic radicals. More preferably, R and R' preferably are selected independently from hydrogen, unsubstituted or substituted $C_1$–$C_{10}$ alkyls, unsubstituted or substituted $C_3$–$C_8$ cycloalkyls, unsubstituted or substituted 3–6 ring member heterocyclic radicals, unsubstituted or substituted $C_6$–$C_{15}$ aryls, or unsubstituted or substituted $C_7$–$C_{11}$ aralkyls. Examples of substituents include halides, $C_1$–$C_6$ alkyls, $C_1$–$C_6$ halogenated alkyls, $C_6$–$C_{15}$ aryls, $C_1$–$C_6$ alkoxys, aminos (primary and secondary), amidos, sulfonates, and hydroxyls.

As a $C_6$–$C_{15}$ aryl, R and R' may be, for example, phenyl, o-tolyl, m-tolyl, p-tolyl, o-xylyl, m-xylyl, p-xylyl, alpha-naphthyl or beta-naphthyl. In a preferred class of aryls, R and R' are selected from $C_6$–$C_8$ aryls or $C_{12}$–$C_{14}$ aryls, and, more preferably, $C_6$–$C_8$ aryls. Any of these groups may contain one or more substituents such as, for example, halides, sulfonates, $C_1$–$C_4$ alkyls, and $C_1$–$C_4$ alkoxys.

As $C_7$–$C_{13}$ aralkyl, R and R' may be, for example, benzyl, 4-methylbenzyl, o-methoxybenzyl, p-methoxybenzyl, diphenylmethyl, 2-phenylethyl, 2-phenylpropyl or 3-phenylpropyl, preferably $C_7$–$C_9$ aralkyl, especially benzyl. As with the alkyls, these groups may contain one or more substituents such as halides, sulfonates, $C_1$–$C_4$ alkyls, $C_1$–$C_4$ alkoxys to form such compounds as para-toluenesulfonic acid (tosylate) and bromobenzenesulfonic acid.

As a $C_1$–$C_{10}$ alkyl, R and R' may be, for example, straight-chain or branched molecules, for example, methyl, ethyl, n-propyl, isopropyl, n-butyl, isobutyl, tert-butyl, n-pentyl, neopentyl, n-hexyl, n-heptyl, n-octyl, or 2-ethylhexyl. In a preferred class of alkyls, R and R' are selected from $C_1$–$C_4$ alkyls. In another preferred class of alkyls, R and R' are branched alkyls, preferably $C_2$–$C_6$ branched alkyls, especially isobutyl. These groups may comprise one or more substituents selected from halogens or $C_1$–$C_4$ alkoxys, especially methoxy, ethoxy, n-propoxy, isopropoxy, n-butoxy, methanesulphonyl, bromine, chlorine or fluorine to form such substituted alkyl groups as methoxymethyl, 2-methoxyethyl, 2-ethoxymethyl, 2-n-butoxyethyl, 3-methoxypropyl, 1-methoxybutyl, 2-methoxybutyl, methanesulphonylmethyl, 2-methanesulphonylethyl, 2-fluoroethyl, 2,2,2-trifluoroethyl, trichloromethyl, 2-chloroethyl, 2-(chloromethyl)ethyl, 2,2,2-trichloroethyl, 2-chloro-n-propyl, methanesulfonic acid, or 3-chloro-n-butyl.

As a $C_3$–$C_8$ cycloalkyl, R and ' may be, for example, cyclopropyl, cyclopentyl, methylcyclopentyl, cyclohexyl, methylcyclohexyl, dimethylcyclohexyl, cycloheptyl or cyclooctyl, preferably cyclohexyl. In a preferred class of cycloalkyl, R and R' are selected from $C_5$–$C_7$ cycloalkyls, and, more preferably, a cyclohexyl. Any of these groups may be substituted with, for example methoxy, ethoxy, n-propoxy, isopropoxy, n-butoxy, chlorine, bromine or As a 3–6 member heterocyclic radical, R and R' may include any known heterocylic atom such as nitrogen and oxygen. Suitable heterocycles include, for example, pyridine, pyran, pyrrole, and furan.

Particularly preferred combinations of Rs are listed in Table 1 below.

TABLE 1

Preferred R and R' Combinations

| No. | R | R' |
|---|---|---|
| 1 | 4-bromophenyl | hydrogen |
| 2 | 3-bromophenyl | hydrogen |
| 3 | 2-bromophenyl | hydrogen |
| 4 | 4-fluorophenyl | hydrogen |
| 5 | 3-fluorophenyl | hydrogen |
| 6 | 2-fluorophenyl | hydrogen |
| 7 | 4-bromo-2-fluorophenyl | hydrogen |
| 8 | 2,4-dibromophenyl | hydrogen |
| 9 | 4-bromo-2-chlorophenyl | hydrogen |
| 10 | 3,5-dichlorophenyl | hydrogen |
| 11 | 4-chlorophenyl | hydrogen |
| 12 | 3-chlorophenyl | hydrogen |
| 13 | 2-chlorophenyl | hydrogen |
| 14 | 2-bromophenyl | methyl |
| 15 | 2-fluorophenyl | 2-fluorophenyl |
| 16 | 2-bromophenyl | 2-bromophenyl |
| 17 | 2-fluorophenyl | methyl |
| 18 | 2-chlorophenyl | methyl |
| 19 | 2-bromophenyl | 2-chlorophenyl |
| 20 | 2-bromophenyl; | 2-fluorophenyl |
| 21 | 2-chlorophenyl | 2-chlorophenyl |
| 22 | phenyl | 2-chlorocyclohexyl |
| 23 | phenyl | chloroethyl |
| 24 | 2-bromophenyl | 2-ethyl propyl |
| 25 | n-butyl | 6-chloropyridyl |
| 26 | 2-chloro-n-propyl | 2-bromocyclohexyl |

In a highly preferred embodiment, one R' is hydrogen and R is a halogenated aromatic, preferably, phenyl, thereby simplifying Formulas (1) and (2) to formulas (3) and (4), respectively, below:

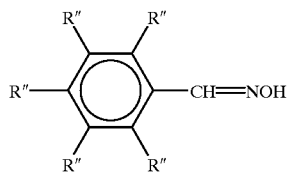

(3)

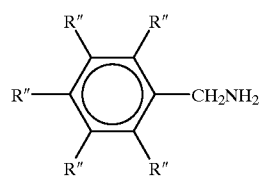

(4)

wherein each R'' is independently selected from hydrogen or a substituent such as a halogen, $C_1$–$C_3$ alkyl, or $C_1$–$C_3$ haloalkyl providing that at least one R'' comprises at least one halogen.

Even more preferably, one to three R''s are selected from either bromine or fluorine and the remainder are hydrogen. Examples of highly preferred halogenated benzylamines include 4-bromobenzylamine and 4-bromo-2-fluorobenzylamine.

In a preferred embodiment, the above-identified oxime starting material may be prepared by oximating its corresponding aldehyde. Such an oximation reaction is known in the art.

In another preferred embodiment, the synthesis method of the present invention is used in hydrogenating a cyclic oxime having a formula:

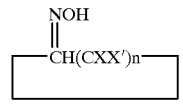

(5)

to form a halogenated amine having the formula:

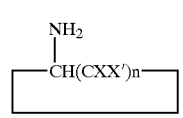

(6)

wherein:

n in an integer no less than 2; and each of X and X' is independently selected from hydrogen, a halogen, or groups as described above with respect to R and R' in Formulas (1) and (2), providing that the ring comprises at least one halogen or a substituent having at least one halogen.

Preferably, n ranges from 2 to 15, and, more preferably from 3 to 10. It is noteworthy to mention that, since n is greater than 1, a plurality of X and X' groups result. Nevertheless, each X and X' is independently selected, such that, for example, various Xs may differ within the same molecule. Particularly preferred ring structures include, for example, 3-chlorocyclohexyl, 2-bromo-9-fluorenyl, 3-chloro-2-norbornanyl, 5-bromo-1-indanyl, 2,7-dibromo-9-fluorenyl, 10,11-dibromodibenzosuberanyl, and 6-bromo-1,2,3,4-tetrahydronaphthyl.

According to the hydrogenation reaction of the present invention, halogenated amines can be obtained in high yield and with high selectivity. For example, in the preparation of 4-bromobenzylamine, the yield is no less than about 70% and, preferably, no less than about 85%, while the selectivity is no less than about 80%, and preferably, no less than about 90%.

The following examples are illustrative of the practice of the present invention.

EXAMPLES

Example 1

This example illustrates a two step preparation of a halogenated benzylamine, specifically, 4-bromobenzylamine. The first step involves the oximation of a halogenated benzaldehyde to produce a halogenated benzaldoxime, and the second step involves the hydrogenation of that oxime to produce the halogenated benzylamine.

Step I: Oximation of 4-bromobenzaldehyde to Form 4-bromobenzaldehyde Oxime

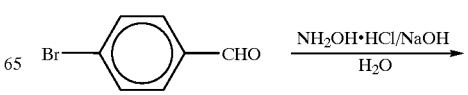

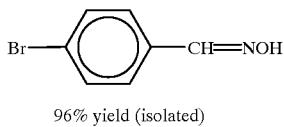

96% yield (isolated)

4-Bromobenzaldehyde (92.5 g, 0.5 mol) was mixed with 200 ml of water in a 1 liter 3-necked round-bottomed flask equipped with a mechanical stirrer and a reflux condenser. The mixture was heated in an oil bath until the aldehyde was completely melted and the oil bath reached a temperature of about 70° C. In a 500 ml Erlenmeyer flask was dissolved 41.7 g of hydroxylamine hydrochloride (0.6 mol) in 200 ml of water while stirring. A solution of sodium hydroxide (24.0 g in 100 ml of water) which was pre-cooled to room temperature was slowly added to the flask while stirring. The resultant solution next was added to the 3 necked round-bottomed flask via an additional funnel over a 30 minute period. A white solid was precipitated in a few minutes once the addition started. The reaction mixture was stirred while maintaining a temperature of 70°. During the entire reaction, a blanket of N2 was maintained over the reaction mixture. After about 3 h, the reaction was completed as indicated by GC analysis. The reaction mixture next was cooled to room temperature and the desired product was collected by vacuum filtration as a white crystalline powder which was dried in a vacuum oven at 80° C. for 15 h. The yield from this reaction was 96.1 g (96%).

Step II: Hydrogenation of 4-bromobenzaldehyde Oxime to Form 4-bromobenzylamine

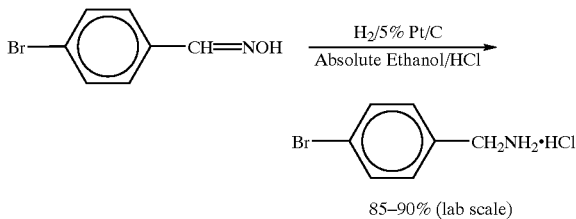

85–90% (lab scale)

The hydrogenation was conducted in a 2 L glass resin kettle having a glass thermocouple well, PFA tubing for ventilation, sampling and H₂ inlet diptubes, fully inert process contact, a polished glass shaft, and a 3' Teflon paddle with an O-ring bearing. To the kettle was added a reaction mixture comprising: 15 g of 5% Pt/C Engelhard 781A-15-1 catalyst (recovered from a previous run for reuse); 62 g of 4-bromobenzaldehyde oxime; and 645 g of 200 proof ethanol containing 6.0% wt HCl gas. During the reaction, the reaction mixture was stirred at 885 rpm at ambient temperature which ranged from 27–29° C. H₂ was fed into the reaction at a pressure of 4–6 psig through an inlet diptube from a 2 L accumulator pressurized to 360 psig. The reaction was monitored by observing pressure drop in the accumulator and periodical sampling for GC analysis. Purification of the reaction product was performed by first vacuum filtering the reaction mixture through a 0.22 μm millpore Teflon-membrane filter to remove the catalyst. Next, the filtrate was concentrated to dryness on a rotary evaporator to afford 66 g of the crude product which in turn was purified by recrystallization in absolute ethanol (total amount of ethanol: 226 g) to afford 48.1 g of purified material (73%).

Concentration of the mother liquor yielded 17.9 g of solid material which was washed with 100 g of ethyl acetate in an ultrasonic bath for 30 minutes to remove the yellow color; the white solid was collected by vacuum filtration to afford 6.4 g of product which was shown to contain predominately the desired compound by ¹H NMR in DMASO-d₆.

What is claimed is:

1. A method of preparing a halogenated amine comprising:
   hydrogenating a halogenated oxime under substantially anhydrous conditions and in the presence of a catalyst comprising a non-palladium noble metal or a base metal under conditions sufficient to produce a halogenated primary amine.

2. The method of claim 1, wherein said catalyst comprises a metal selected from the group consisting of iridium, rhodium, ruthenium, platinum, nickel, cobalt, oxides thereof, and combinations of two or more thereof.

3. The method of claim 2, wherein said catalyst comprises platinum and/or oxides thereof.

4. The method of claim 1, wherein said catalyst comprises a support of either charcoal or aluminum.

5. The method of claim 1, wherein said catalyst comprises about 1 to about 10 % metal by weight.

6. The method of claim 1, wherein said catalyst comprises about 1 to about 10 % platinum by weight deposited on a charcoal support, and wherein the concentration of catalyst to starting material is about 0.5 to about 4% by weight.

7. The method of claim 1, wherein said method further comprises:
   recovering said catalyst; and
   optionally reusing said catalyst to catalytically hydrogenate another halogenated oxime.

8. The method of claim 1, wherein the step of hydrogenating an oxime is conducted at about atmospheric pressure and at about room temperature.

9. The method of claim 1, wherein the step of hydrogenating the oxime is conducted in the presence of an organic solvent.

10. The method of claim 1, wherein the step of hydrogenating the oxime is conducted in the presence of an inorganic acid.

11. The method of claim 1, wherein the step of hydrogenating said oxime is conducted in a non-ferrous reactor.

12. The method of claim 11, wherein the reactor comprises glass.

13. The method of claim 1, wherein the step of hydrogenating said oxime comprises combining said amine such that it does not poison said catalyst.

14. The method of claim 1, wherein said halogenated oxime has the formula:

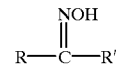

and said halogenated amine has the formula:

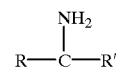

wherein:
   R and R' are independently selected from hydrogen, unsubstituted or substituted aliphatic radicals, or an unsubstituted or substituted aromatic radicals, providing that R or R' comprises at least one halogen.

15. The method of claim 14, wherein R and ' are selected independently from the group consisting of hydrogen, unsubstituted or substituted $C_1$–$C_{10}$ alkyls, unsubstituted or substituted $C_3$–$C_8$ cycloalkyls, unsubstituted or substituted 3–6 ring member heterocyclic radicals, unsubstituted or substituted $C_6$–$C_{15}$ aryls, and an unsubstituted or substituted $C_7$–$C_{11}$ aralkyls; wherein substituents are selected from the group consisting of halides, $C_1$–$C_6$ alkyls, $C_6$–$C_{15}$ halogenated alkyls, $C_6$–$C_{15}$ aryls, $C_1$–$C_6$ alkoxys, nitros, aminos, amidos, sulfonates, and hydroxyls.

16. The method of claim 1, wherein said halogenated oxime has the formula:

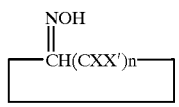

and said halogenated amine has the formula:

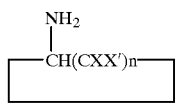

wherein:
n in an integer no less than 2; and
each X and X' is independently selected from hydrogen, a halogen, an unsubstituted or substituted aliphatic radical, or an unsubstituted or substituted aromatic radical, providing that the ring comprises at least one halogen or a substituent having at least one halogen.

17. A method of preparing a halogenated benzylamine comprising:
hydrogenating a halogenated benzaldoxime wherein the step of hydrogenating the oxime is conducted under substantially anhydrous conditions and in the presence of a catalyst comprising a non-palladium noble metal or a base metal under conditions sufficient to form a halogenated benzylamine.

18. The method of claim 17, wherein said catalyst comprises platinum.

19. The method of claim 18, wherein said method further comprises:
recovering said catalyst; and
optionally hydrogenating another halogenated benzaldoxime in the presence of said catalyst under conditions sufficient to form a halogenated benzylamine.

20. The method of claim 18, further comprising:
oximating a halogenated benzaldehyde to form said halogenated benzaldoxime.

21. The method of claim 18, wherein the step of hydrogenating said halogenated benzaldoxime is conducted at about atmospheric pressure and at about room temperature.

22. The method of claim 18, wherein the step of hydrogenating said halogenated benzaldoxime is conducted in a reaction mixture comprising an organic solvent and an acid.

23. The method of claim 22, wherein said reaction mixture comprises absolute ethanol and hydrogen chloride.

24. The method of claim 18, wherein said halogenated benzylamine is selected from the group consisting of 4-bromobenzylamine and 4-bromo-2-fluorobenzylamine.

25. The method of claim 1, wherein the yield is no less than about 70% and the selectivity is no less than about 80%.

26. The method of claim 25, wherein the yield is no less than 85% and the selectivity is no less than about 90%.

* * * * *